United States Patent
Sarngadharan et al.

(10) Patent No.: US 6,503,736 B1
(45) Date of Patent: Jan. 7, 2003

(54) ANTIBODIES TO CROSSLINKERS AND METHODS FOR USING THE SAME

(75) Inventors: Mangalasseril G. Sarngadharan, McLean, VA (US); Ranajit Pal, Gaithersburg, MD (US); Anthony L. DeVico, Alexandria, VA (US)

(73) Assignee: bioMérieux, Inc., Hazelwood, MO (US)

( * ) Notice: Subject to any disclaimer, the term of this patent is extended or adjusted under 35 U.S.C. 154(b) by 0 days.

(21) Appl. No.: 09/438,895

(22) Filed: Nov. 12, 1999

(51) Int. Cl.⁷ .................. C12P 21/08; C07K 16/00; C07K 1/00
(52) U.S. Cl. ............... 435/70.21; 530/388.21; 530/388.9; 530/809
(58) Field of Search ............ 530/388.21; 435/70.21

(56) References Cited

U.S. PATENT DOCUMENTS

| | | |
|---|---|---|
| 3,855,208 A | 12/1974 | Rutner |
| 5,344,757 A | 9/1994 | Holtke |
| 5,354,657 A | 10/1994 | Holtke |
| 5,518,723 A * | 5/1996 | DeVico et al. |
| 5,559,039 A | 9/1996 | Williams |
| 5,747,244 A | 5/1998 | Sheridan et al. |
| 5,804,371 A | 9/1998 | Hoss |
| 5,843,454 A | 12/1998 | Devico et al. |
| 5,843,670 A | 12/1998 | Suzuki |
| 5,922,534 A | 7/1999 | Lichtenwalter |
| 5,929,108 A | 7/1999 | Lubberding |

FOREIGN PATENT DOCUMENTS

| WO | WO99/02266 | 1/1999 |
|---|---|---|

OTHER PUBLICATIONS

Kuby et al, 1994, Immunology, Second edition, pp. 85–96.*
Colman et al, Effects of amino acid sequence changes on antibody–antigen interaction, 1994, A structural view of immune recognition by antibodies, pp. 33–36.*
Devico, A.L. et al., "Monoclonal antibodies raised against covalently crosslinked complexes of human immunodeficiency virus type 1 gp120 and CD4 receptor identify a novel complex–dependent epitope on gp120," *Virology*, 1995, 211:583–588.

* cited by examiner

*Primary Examiner*—Christina Chan
*Assistant Examiner*—Phuong N. Huynh
(74) *Attorney, Agent, or Firm*—Rothwell, Figg, Ernst & Manbeck, p.c.

(57) ABSTRACT

The present invention is directed to the discovery of antibodies that will react to proteins or nucleic acids bound to particular crosslinkers, but not to the free crosslinkers or free proteins or nucleic acids. Monoclonal antibodies with such binding specificity have widespread applications in receptor-ligand binding, immunodiagnostic and nucleic acid diagnostics.

3 Claims, 1 Drawing Sheet

—— Negative Control
·········· Anti-BS3 Antibody
—— Anti-gp120-CD4 Complex Specific Antibody (8F101)
- - - - Anti-gp120 Antibody (M77)

ANTIBODIES TO CROSSLINKERS AND METHODS FOR USING THE SAME

FIELD OF THE INVENTION

The present invention is directed to the discovery of antibodies that will react to proteins or nucleic acids bound to particular crosslinkers, but not to the free crosslinkers or free proteins or nucleic acids. Monoclonal antibodies with such binding specificity have widespread applications in receptor-ligand binding, immunodiagnostic, molecular amplification assays and other nucleic acid diagnostics.

BACKGROUND OF THE INVENTION

DSS (Dissuccinimidyl suberate) is a non-cleavable, membrane permeable, amine-reactive, homobifunctional crosslinker. BS3 (Bis[Sulfosuccinimidyl]suberate) is a non-cleavable, membrane impregnable, water soluble analog of DSS. By means of two bifunctional sulfo-NHS ester reactive groups, BS3 (and DSS) can serve as a crosslinking reagent between molecules with amino groups. The BS3 and DSS compounds are sold by Pierce (Rockford, Ill.) as protein crosslinking reagents. These compounds will crosslink molecules that are within a certain distance (i.e. spacer arm length), but otherwise will modify such molecules without necessarily crosslinking them. Thus, BS3 and DSS can be used as labels of analytes.

Such modifications of proteins and nucleic acids by digoxigenin, for instance, are known in the art. In general, digoxigenin has been used as a label in bioanalytical assays where it may be itself radiolabelled or may act as a hapten, for instance, which reacts with an anti-hapten antibody for detection of the digoxigenin-labeled analyte. See U.S. Pat. Nos. 3,855,208; 5,198,537; and 5,804,371.

Digoxigenin and derivatives thereof have also been used in the field of nucleic acid diagnostics, where in general it is incorporated as a label into amplificates or probes, and whereby the labelled moieties are detected by hapten anti-hapten reaction principle. See, for example, U.S. Pat. Nos. 5,354,657; 5,843,670; 5,929,108; and 5,344,757.

However, there are drawbacks of the digoxigenin system. First, the procedure for derivatizing with digoxigenin is relatively complicated. Second, because digoxigenin is a large molecule and contains a hydrophobic steroid, modification of a molecule will perturb the molecule's conformation. Third, digoxigenin is relatively expensive, as compared to for instance BS3.

Therefore, a need exists for a simpler bioanalytical detection system, which does not require multiple derivatization steps, is less expensive, and is less likely to disrupt the conformation of the molecule being modified therewith. A system which is parallel in many respects to the digoxigenin system has now been, unexpectedly, discovered. This system can be used in the same manner as digoxigenin.

SUMMARY OF THE INVENTION

The present invention is the result of the discovery that certain monoclonal antibodies produced by hybridomas raised against BS3-modified gp120-CD4 complexes were actually directed to the BS3 linker itself. These antibodies do not react with the free BS3 molecule alone, and show different binding specificities. For instance, some of the antibodies appear to react with the "hinge" formed between amino acid residues and the BS3 molecule in a modified protein. These antibodies would be expected to crossreact with proteins treated with other crosslinkers, such as DSG (Pierce) and DTSSP (a molecule analogous to DSS but with an S—S bridge in the middle of the methylene chain). Other monoclonals react with the linear carbon chain that lies between the two end sulfosuccinimidyl groups of the BS3 molecule. Thus, such monoclonals would also be expected to react with DSS modified (or crosslinked) proteins, because it contains the same long methylene chain, and presumably other crosslinkers such as DMP, DMA, DSG and MSA (all sold by Pierce).

The monoclonals of the present invention are useful in diagnostic immunoassays, such as ELISAs. They are also useful in ligand-receptor studies. Finally, it is also contemplated that the BS3anti-BS3 system can be used as a detection system for nucleic acid amplification assays. In fact, these anti-hapten antibodies can be used in the same manner as other hapten/anti-hapten systems known in the art, such as digoxigenin/anti-digoxigenin.

DETAILED DESCRIPTION OF THE INVENTION

Figure 1A:
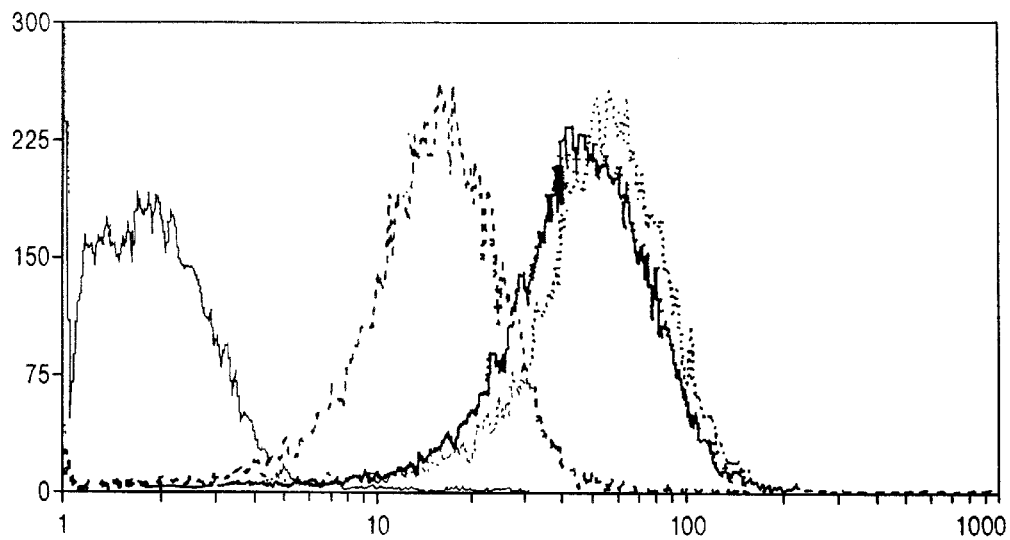
FIG. 1 shows the FACS profile on the binding of BS3 labeled gp120 to the Sup T1 cell membrane (Panel A) and the binding of unmodified gp120 to SUP T1 cells (Panel B).

The term "anti-BS3" in reference to the antibodies of the present invention is not meant to imply that these antibodies are only reactive with BS3-modified molecules, but as explained above, are likely to be reactive with other known crosslinkers used to modify proteins or nucleic acids. In addition, in the present specification the term "BS3-modified" includes molecules modified by the other crosslinkers mentioned above as being crossreactive with the antibodies. Because of their close similarity, BS3 and DSS are particularly preferred in the present invention.

BS3 (Bis[Sulfosuccinimidyl]suberate) is a crosslinker which contains two bifunctional sulfo-NHS ester reactive groups. See formula below.

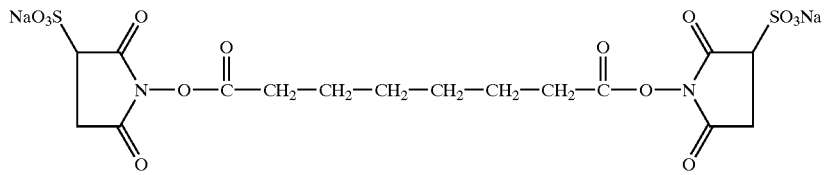

DSS (Disuccinimidyl suberate) is a water insoluble analogue of BS3, and has the formula below.

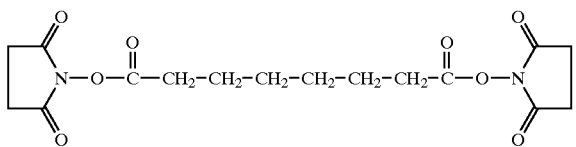

When these crosslinkers are reacted with molecules containing amino groups, the succinimidyl groups on each end of the molecule are cleaved, leaving essentially a 6 carbon fatty acid chain, either between two molecules that are being crosslinked or extending from the modified molecule. This is diagrammatically depicted below.

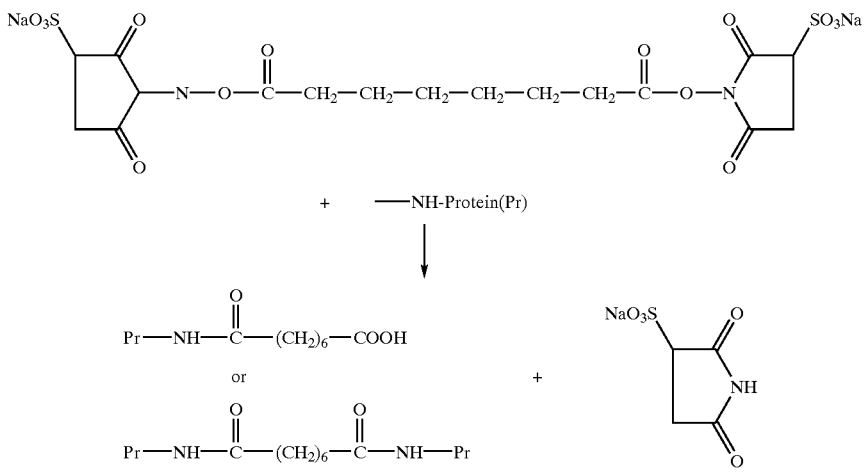

In studies involving HIV, BS3 was used to crosslink a complex of HIV-1 gp120 envelope protein and soluble human CD4. This covalently crosslinked complex was then used to immunize mice for the purposes of generating complex specific monoclonal antibodies (mABs). Although several complex specific mABs were generated from the immunized mice, several IgG and IgA hydridomas were produced which are specific for the BS3 component of the complex. Interestingly, none of the monoclonals were reactive with gp120, sCD4 (soluble CD4), or free BS3; the reactivity was specific for BS3 linked to an amino group.

In its preferred embodiment, this invention is directed to four murine hydridomas that secrete monoclonal antibodies with unique specificity. Chemical modification of proteins with BS3 resulted in the exposure of an epitope in the protein or in the BS3, which showed strong immunoreactivity with these antibodies. One of the monoclonals is an IgA (designated 7E3-2E7), and three others are IgGs (2C3-2E10, 12G9-2C5, and 11F2-2F7). These monoclonals react with BS3 linked to proteins other than gp120CD4, and thus have broad utility is the assay arts.

The hybridomas producing the antibodies have the same designations as the monoclonals above, and all four were deposited with the American Type Culture Collection (ATCC), 10801 University Blvd., Manassas, Va., 20110-2209, USA, under the terms of the Budapest Treaty, on Nov. 11, 1999, and given ATCC the designations: PTA-936 for 7E3-2E7, PTA-934 for 2C3-2E10, PTA-935 for 12G9-2C5 and PTA-937 for 11F2-2F7.

The IgA (7E3-2E7) monoclonal is particularly unique and preferred because of its five binding sites. It can thus amplify the signal in an immunoassay. It is also particularly useful in a two antibody system, as a capture antibody. That is, anti-BS3 IgA can be used as a capture antibody for all BS3-modified antigens in a sample. An IgG probe antibody can be added which is specific for a particular antigen that has been captured. Then, a labeled anti-IgG detector antibody can be added, which will not bind to the IgA capture antibody.

Other monoclonal antibodies may be made by methods well known in the art. See, for instance, Harlow and Lane, ANTIBODIES: A LABORATORY MANUAL, Cold Spring Harbor Laboratory (1988), ISBN 0-87969-314-2, which is incorporated herein by reference. The immunogen in such methods would be the crosslinker-modified molecule.

Additionally, the term "antibody" is intended to also encompass fragments, such as the Fab, Fab', F(ab)$_2$ and F(ab')$_2$ fragments, or other antibody fragments modified, for example, by genetic engineering.

For the assay of protein analytes, a free amino group can be reacted with the BS3, in the manner set forth in, for instance, Example 1. Once labelled, these proteins can be detected with anti-BS3 antibodies, which will specifically bind with the methylene spacer of the BS3 or the "hinge" between the protein and the BS3 molecule (i.e., the part containing the C=O group). The antibodies themselves can be labelled with a conventional label, such as an enzyme, fluorescent, chromogenic, metal particle or radioactive label, or can be detected using a labeled anti-IgA or anti-IgG antibody.

Essentially, any method in which the digoxigenin/anti-digoxigenin system can be employed in the field of antigen assay is also a method in which the BS3/anti-BS3 can be used. In this regard, U.S. Pat. Nos. 3,855,208, 5,804,371, and 5,843,670, which disclose various assays with digoxigenin/anti-digoxigenin, are incorporated by reference.

In one embodiment, the BS3/anti-BS3 system is useful in diagnostic immunoassays that employ two antibodies (the capture antibody and the detector antibody). In these assays, the detector antibody is treated with BS3 and any unreacted BS3 is blocked. The BS3-conjugated antibody bound to the antigen that has been captured by the capture antibody can be recognized by an anti-BS3 antibody that contains a label, such as HRP. It is contemplated that this assay system would have an increased senstivity over an ELISA using two murine monoclonal antibodies and a secondary anti-mouse antibody-enzyme conjugate, because the secondary antibody will also react with the capture antibody on the solid phase. See further, above, regarding the IgA antibody of the present invention.

The relevance for nucleic acid diagnostics of the anti-BS3 mABs is as a detection reagent. Given the reactivity of BS3 to dNTPs or rNTPs with amino groups, the same chemical process that is used for protein labeling/crosslinking can be used. Once the nucleotide is modified with the BS3, it can still serve as a monomer in a nucleic acid polymerization reaction, and the resulting product would be reactive with the anti-BS3 mABs. The bound Ab can then be detected either with an appropriately labeled second Ab, or by incorporating a label into the anti-BS3 Ab directly. Essentially, any DNA detecting method in which the digoxigenin/anti-digoxigenin system can be employed is also a method in which the BS3/anti-BS3 can be used. In this regard, the nucleic acid detection assays disclosed in U.S. Pat. Nos. 5,843,670, 5,198,537, 5,354,657, 5,843,670, 5,929,108 and 5,344,757 are incorporated by reference.

Experiments have been conducted on this aspect of the invention by making dGTP monomer complexes with BS3, which were then used in an in vitro transcriptase reaction on a polyc template. The product was transferred to nitrocellulose and analyzed in Western Blot-type analysis with anti-BS3. The product was successfully detected by this method, indicating that (1) dGTP can be labeled with BS3, and (2) the modified dGTP can serve as a reactive monomer for reverse transcription.

Several formats are envisaged in a nucleic acid diagnostic system using these monoclonals. First, BS3 modified NTP's (those containing an amino group, or else modified to contain an amino group) could be used as monomers in an amplification reaction (such as PCR, NASBA, etc.). The monomers would be incorporated into the amplicons (amplificates), which can then be detected with the anti-BS3 antibodies. Second, one could modify the 5' end with the P2 primer in a transcription based amplification reaction such as NASBA, which in combination with the monoclonals can be a generic capture method. Third, modification of the 5' end of a known capture probe and using the monoclonal to a linker between a particle or solid substrate as a means to bind the capture probe to the surface. Fourth, nucleic acid can be labelled with the BS3 (or other crossreactive crosslinker) and used as a probe for hybridization. The nucleic acid to be assayed can be detected by allowing it to hybridize with the probe to form a nucleic acid hybrid, removing the free probe from the system, and detecting the label contained in the hybrid. In the present invention, the BS3 label can be detected using an enzyme-bound anti-BS3 antibody. The nucleic acid to be assayed is usually immobilized on a membrane or nitrocellulose prior to use.

For hybridization in the nucleic acid detection method of the present invention, any common hybridization method can be used, including colony hybridization, plaque hybridization, dot blot hybridization, southern or northern hybridization, and the like. The nucleic acid to be assayed may be either DNA or RNA. The nucleic acid probe may also be DNA or RNA.

Other, even more sophisticated uses of the monoclonal antibodies would be apparent to those skilled in the art.

The monoclonal antibodies of the present invention are also superior in that they can be used in column purification of molecules. For instance, an anti-BS3 column can be used to purify BS3 (or other crossreactive crosslinker) modified proteins/nucleic acids from a mixture thereof. In addition, in an immunoassay system that uses two mouse monoclonals, for instance, one could not use a labelled antimouse antibody to detect complex formation. However, one of the mouse antibodies could be labelled with BS3, and then detected with a labeled anti-BS3 antibody.

The following examples are not intended to limit the scope of the present invention.

EXAMPLE 1

Preparation of Monoclonal Antibodies Reacting to BS3 Modified Protein

Hybridomas secreting BS3 specific antibodies were isolated from mice immunized with BS3 crosslinked HIV-1 gp120-CD4 complexes. Equimolar quantities of purified gp120 from an HIV-1$_{IIIB}$ isolate and recombinant soluble CD4 were incubated at 37° C. for 60 min. in PBS. A stock solution of BS3 (5 mM) was prepared in distilled water. Physically associated complex formed after such incubation was crosslinked by adding BS3 to a final concentration of 0.5 mM. The solution was incubated for 30 min at room temperature and unreacted BS3 was blocked by adding Tris buffer (pH 8.0) to a final concentration of 50 mM.

Five mice were immunized with BS3 labeled gp120-CD4 complex (20 ug/mouse) in complete Freund's adjuvant. Subsequent immunizations were administered in incomplete Freund's adjuvant until the animals developed high titered antibody response against gp120 and CD5. Splenic lymphocytes from these immunized animals were fused with NS1 cells and the hybridomas resulting from such fusion were screened against uncrosslinked and BS3 cross-linked gp120-CD4 complex. Single cell cloning of such hybridomas reacting specifically with BS3 cross-linked complex resulted in the isolation of four stable hybridomas as shown below:

TABLE 1

| Hybridomas Clone | Isotype |
| --- | --- |
| 7E3-2E7 | IgA |
| 2C3-2E10 | IgG1 |
| 12G9-2C5 | IgG1 |
| 11F2-2F7 | IgG1 |

Supernatant from these hybridoma clones were tested at different dilutions for immunological reactivity against BS3-linked and unlinked gp120-CD4 complex by ELISA and the results (expressed as optical density at 450 nm) are shown below:

TABLE 2

| Hybridoma Clone | Hybridoma supernatant reacted with BS3-crosslinked gp120-CD4 complex at dilutions | | | Hybridoma supernatant reacted with uncrosslinked gp120-CD4 complex at dilutions | | |
| --- | --- | --- | --- | --- | --- | --- |
| | Undiluted | 1:1 | 1:10 | Undiluted | 1:1 | 1:10 |
| 7E3-2E7 | >3.00 | >3.00 | >3.00 | 0.125 | 0.108 | 0.105 |
| 2C3-2E10 | 2.741 | 2.728 | 2.486 | 0.125 | 0.120 | 0.095 |
| 12G9-2C5 | 2.644 | >3.00 | 2.885 | 0.095 | 0.097 | 0.086 |
| 11F2-2F7 | 2.824 | >3.00 | 2.728 | 0.252 | 0.104 | 0.091 |

It is clear from the results presented above that the antibodies secreted from these hybridoma clones react specifically with BS3-crosslinked gp120-CD4 complex and had no reactivity with uncrosslinked complex.

In order to determine whether these antibodies will react with other proteins labeled with BS3, a 5% solution of dry milk in PBS was coated onto an ELISA plate. After binding the proteins for 60 min at 37° C., the wells were treated with 0.5 mM BS3 for 30 min at room temperature. Unreacted BS3 was then blocked with Tris buffer as described above and the wells were reacted with the supernatant from the four hybridoma clones listed above and also with a hybridoma secreting non-BS3 antibody (8F10-2E11). As shown below, all four supernatants exhibited strong reactivity with BS3-modified dried milk proteins. However as expected, no reactivity was observed with the non-BS3 antibody.

TABLE 3

Immunoreactivity of anti-BS3 antibodies to BS3 modified 5% Dry Milk Solution in PBS (Blotto)

| Hybridoma Clone | ELISA reactivity of different dilutions of hybridoma supernatant in duplicate (Optical Density 450 nm) | | | | |
|---|---|---|---|---|---|
| | Undiluted | 1:1 | 1:20 | 1:200 | 1:2000 |
| 12G9 | >3.00, >3.00 | >3.00, >3.00 | >3.00, >3.00 | >3.00, >3.00 | 0.406, 0.383 |
| 7E3 | >3.00, >3.00 | >3.00, >3.00 | >3.00, >3.00 | >3.00, >3.00 | 1.574, 1.611 |
| 2C3 | >3.00, 2.803 | 2.683, 2.774 | 1.417, 1.160 | 0.284, 0.236 | 0.090, 0.079 |
| 11F2 | >3.00, >3.00 | >3.00, >3.00 | 0.812, 0.857 | 0.138, 0.141 | 0.067, 0.068 |
| DMEM Medium (Negative control) | 0.052, 0.052 | Not Tested | Not Tested | Not Tested | Not Tested |
| Unrelated Hybridoma (8F101) (Negative control) | 0.170, 0.169 | Not Tested | Not Tested | Not Tested | Not Tested |

EXAMPLE 2

Application of Anti-BS3 Antibodies

1. Receptor—Ligand Binding Study

A BS3/anti-BS3 system will have useful applications in the area of receptor-ligand binding assays. Such assays can be performed both on solid phase ELISA format and on the cell surface. For binding assays on cell surface, BS3-linked ligand will be reacted with cells expressing its receptor. The binding of BS3-labeled ligand to the cell surface will then be detected using anti-BS3 monoclonal antibody followed by anti-mouse IgG conjugated to FITC. Binding of FITC conjugated antibody to the cell surface ben be detected either by flow cytometry or by immunofluorescence assay. An example of such binding assay using BS3-linked ligand is described below:

Binding of HIV-1 gp120 to its receptor CD4 on the cell surface was examined using anti-BS3 antibody. Purified gp120 was labeled with BS3 by incubating purified protein with 0.5 mM BS3 in PBS at room temperature for 30 min. Unreacted BS3 was blocked by adding Tris buffer (pH 8.0) to a final concentration of 50 mM. The labeled protein was then incubated with Sup T1 cells at 4° C. for 30 min. Sup T1 cells have been shown to express high level of CD4 on the cell surface and are highly susceptible to HIV-1 infection.

Cells were then washed with PBS and reacted with anti-BS3 antibody for 30 min at 4° C.

Figure 1B:
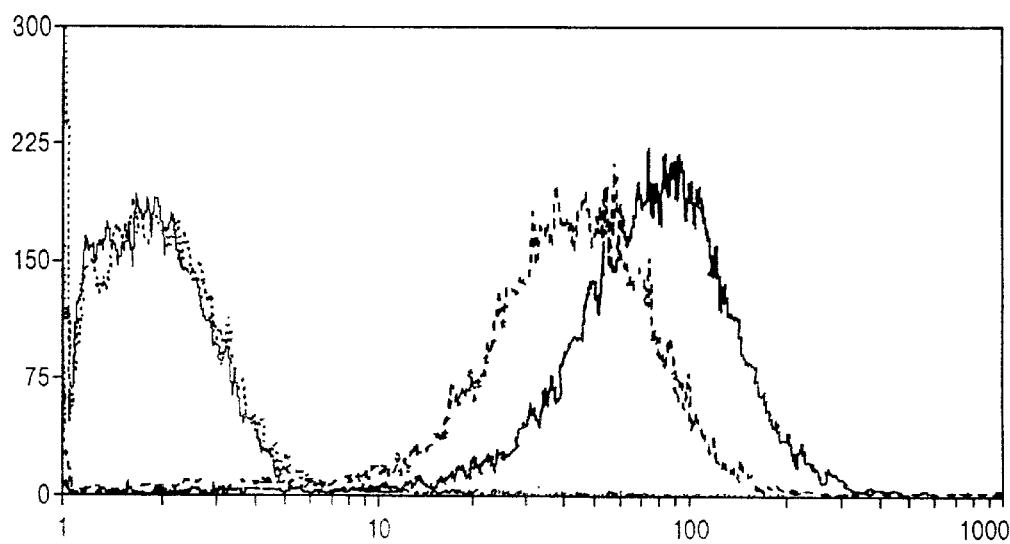

The binding of anti-BS3 antibody to the cell surface was detected using FITC conjugated goat anti-mouse antibody. FIG. 1A shows the FACS profile on the binding of BS3 labeled gp120 to the sup T1 cell membrane. Binding of unmodified gp120 to Sup T1 cells was also examined for comparison (FIG. 1B). It is clear from the figure that the binding of BS3-labeled gp120 to CD4 exposes a complex-specific epitope recognized by the monoclonal antibody 8F101. This experiment further demonstrates that the modification of gp120 with BS3 did not affect the binding specificity of the glycoprotein. In addition, an anti-V3 loop monoclonal antibody (M 77) also reacted with BS3-labeled gp120 bound to the cell surface.

Receptor ligand binding can also be performed by solid phase ELISA using BS3/anti-BS3 system. In this assay the receptor can be absorbed on a solid phase plastic surface and can be then reacted with BS3-labeled ligand. The binding of BS3 labeled ligand to the receptor can be detected using anti-BS3 antibody followed by an HRP-conjugated goat anti-mouse antibody.

EXAMPLE 3

Immunodiagnostic Assays

Another utility of a BS3/anti-BS3 system will be in the area of immunodiagnostic assays that use a two-antibody detection system. In this assay the capture antibody coated on a plate will be used to capture the antigen to be detected. The BS3 labeled detector antibody will be reacted with the antigen captured on the plate by the capture antibody. An anti-BS3 that is conjugated with a label such as HRP can then recognize BS3 labeled detector antibody bound to the antigen. Using anti-BS3 antibody it will thus be possible to design an assay using two mouse antibodies at the same time. It is anticipated that the antigen capture assay using BS3 labeled detector antibody will have an increased sensitivity over an ELISA which uses two murine monoclonal antibodies and a secondary anti-mouse antibody-enzyme conjugate.

We claim:

1. A monoclonal antibody that will specifically binds to a crosslinker moiety of a BS3 or DSS crosslinked protein or nucleic acid, but not to free BS3 or DSS or to uncrosslinked protein or nucleic acid.

2. The monoclonal antibody of claim 1, which is selected from the group consisting of: 7E3-2E7 produced by hybridoma 7E7 (ATCC Accession No. PTA-936); 2C3-2E10 produced by hybridoma 2C3-2E10 (ATCC Accession No. PTA-934); 12G9-2C5 produced by hybridoma 12G9-2C5 (ATCC Accession No. PTA-935); and 11F2-2F7 produced by hybridoma 11F2-2F7 (ATCC Accession No. PTA-937).

3. The monoclonal antibody of claim 1 that specifically binds to a crosslinked moiety of BS3 DSS crosslinked protein.

* * * * *